United States Patent [19]

Mackaness et al.

[11] 4,307,099
[45] Dec. 22, 1981

[54] REACTION PRODUCTS OF PYRAZOLO[1,5-C]QUINAZOLINE DERIVATIVES AND PROLINE DERIVATIVES AND METHODS FOR REDUCING BLOOD PRESSURE WHILE INHIBITING ALLERGIC REACTIONS WITH THEM

[75] Inventors: George B. Mackaness, Princeton; Kathryn A. Losee, New Brunswick, both of N.J.

[73] Assignee: E. R. Squibb & Sons, Inc., Princeton, N.J.

[21] Appl. No.: 162,861

[22] Filed: Jun. 25, 1980

[51] Int. Cl.³ ............... A61K 31/505; C07D 487/04
[52] U.S. Cl. ................................ 424/251; 544/250
[58] Field of Search ........................ 424/251; 544/250

[56] References Cited

U.S. PATENT DOCUMENTS 3,108,106 10/1963 Maillard .................. 424/260 X
4,105,776 8/1978 Ondetti et al. ............... 424/274
4,112,096 9/1978 Vogt ........................ 424/251

Primary Examiner—Donald G. Daus
Assistant Examiner—Diana G. Rivers
Attorney, Agent, or Firm—Lawrence S. Levinson; Burton Rodney

[57] ABSTRACT

Compounds of the following structure are provided

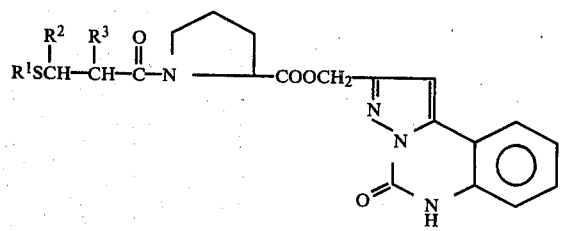

wherein $R^1$ is hydrogen or lower alkanoyl, $R^2$ is hydrogen or lower alkyl, and $R^3$ is hydrogen, lower alkyl or trifluoromethyl. The above compounds have useful hypotensive activity and anti-allergy activity.

9 Claims, No Drawings

REACTION PRODUCTS OF PYRAZOLO[1,5-C]QUINAZOLINE DERIVATIVES AND PROLINE DERIVATIVES AND METHODS FOR REDUCING BLOOD PRESSURE WHILE INHIBITING ALLERGIC REACTIONS WITH THEM

BACKGROUND OF THE INVENTION

U.S. Pat. No. 4,105,776 discloses proline derivatives and related compounds having the formula

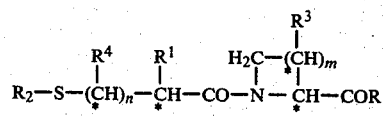

wherein

R is hydroxy, $NH_2$ or lower alkoxy;

$R_1$ and $R_4$ each is hydrogen, lower alkyl, phenyl or phenyl-lower alkyl;

$R_2$ is hydrogen, lower alkyl, phenyl, substituted phenyl wherein the phenyl substituent is halo, lower alkyl or lower alkoxy, phenyl-lower alkyl, diphenyl-lower alkyl, triphenyl-lower alkyl, lower alkylthiomethyl, phenyl-lower alkylthiomethyl, lower alkanoyl-amidomethyl,

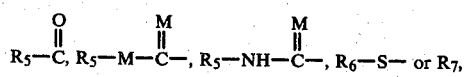

$R_3$ is hydrogen, hydroxy or lower alkyl;

$R_5$ is lower alkyl, phenyl or phenyl-lower alkyl;

$R_6$ is lower alkyl, phenyl, substituted phenyl (wherein the phenyl substituent is halo, lower alkyl or lower alkoxy), hydroxy-lower alkyl or amino(carboxy)-lower alkyl;

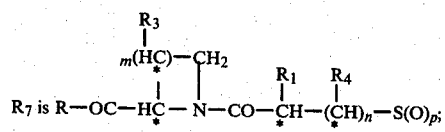

M is O or S;

m is 1 to 3;

n and p each is 0 to 2, and to processes for making them.

The asterisks indicate asymmetric carbon atoms. Each of the carbons bearing a substituent $R_1$, $R_3$ and $R_4$ is asymmetric when that substituent is other than hydrogen.

The above compounds are useful as inhibitors of the conversion of the decapeptide angiotensin I to angiotensin II and thus are useful in reducing or relieving angiotensin related hypertension.

U.S. Pat. No. 4,112,096 discloses 2-(hydroxymethyl)-pyrazolo[1,5—c]quinazolin-5-one which has the structure

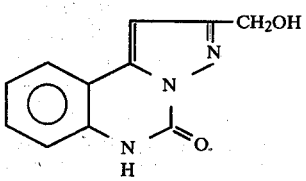

This compound is useful in treating allergic conditions.

DESCRIPTION OF THE INVENTION

The present invention relates to compounds of the structure

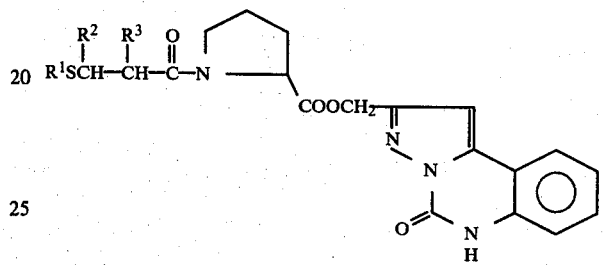

wherein $R^1$ is hydrogen, or lower alkanoyl, $R^2$ is hydrogen or lower alkyl, and $R^3$ is hydrogen, lower alkyl or trifluoromethyl.

The lower alkyl groups represented by any of the variables include straight and branched chain hydrocarbon radicals having from one to seven carbons, that is from methyl to heptyl, for example, methyl, ethyl, propyl, isopropyl, butyl, isobutyl, t-butyl, pentyl, isopentyl and the like. The $C_1$–$C_4$ members, especially $C_1$ and $C_2$ members are preferred.

The lower alkanoyl groups are those having the acyl radicals of the lower ($C_2$–$C_7$) fatty acids, for example, acetyl, propionyl, butyryl, isobutyryl and the like. Similarly, those lower alkanoyl groups having up to four carbons, and especially acetyl, are preferred.

Most preferred are compounds of Formula I wherein $R^1$ is hydrogen, $R^2$ is hydrogen and $R^3$ is hydrogen.

The compounds of Formula I are useful as hypotensive agents. They inhibit the conversion of the decapeptide angiotensin I to angiotensin II and, therefore, are useful in reducing or relieving angiotensin related hypertension. The action of the enzyme renin on angiotensinogen, a pseudo-globulin in blood plasma, produces angiotensin I. Angiotensin I is converted by angiotensin converting enzyme (ACE) to angiotensin II. The latter is an active pressor substance which has been implicated as the causative agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one, or a combination of compounds, of Formula I angiotensin dependent hypertension in the species of mammal suffering therefrom is alleviated.

The compounds of Formula I are also useful in treating various allergic conditions in mammalian species such as mice, cats, dogs, etc. They are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7:238-248 (1972), for a discussion of the predictability of clinical efficacy of compounds active in the PCA). The compounds can be used prophylactically or therapeutically to treat various allergic and immunological disorders and in particular to treat certain types of asthma, hay-fever, and rhinitis.

It will also be appreciated that the compounds of the invention will thus be useful in lowering blood pressure while causing little or no allergic reactions to same.

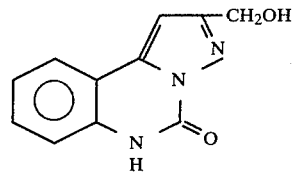

which is described in U.S. Pat. No. 4,112,096.

Thus, in forming the compounds of Formula I, the Formula II acid is reacted with the Formula III alcohol in the presence of a coupling agent, such as dicyclohexylcarbodiimide or the like and in the presence of an organic base, such as 4-methylaminopyridine, to form a compound of the structure

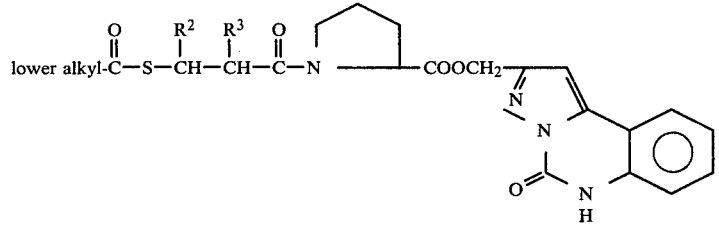

A single dose, or preferably two to four divided daily doses, provided on a basis of about 0.1 to 100 mg per kilogram of body weight per day, preferably about 1 to 15 mg per kilogram of body weight per day is appropriate to reduce blood pressure without sustaining allergic reactions. The substance is preferably administered orally, but parenteral routes such as the subcutaneous, intramuscular, intravenous or intrapertioneal routes can also be employed.

The compounds of Formula I can be formulated for use in the reduction of blood pressure while inhibiting and alleviating allergic conditions in compositions such as tablets, capsules or elixirs for oral administration or in sterile solutions or suspensions for parenteral administration. About 10 to 500 mg of a compound or mixture of compounds of Formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of Formula I of this invention can be obtained utilizing as starting materials proline derivatives having the formula

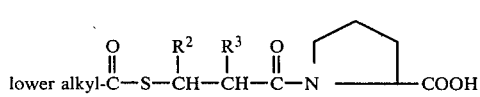

which are described in U.S. Pat. No. 4,105,776 and 2-(hydroxymethyl)pyrazolo[1,5—c]quinazolin-5-one The lower alkanoyl protecting group in the Formula Ia compound may be removed by ammonolysis, for example, by reaction with methanolic ammonia, to form the product of the invention

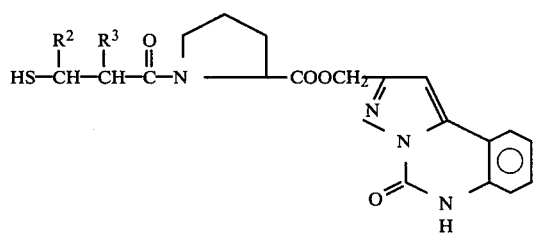

In carrying out the above reaction, each of the compounds of Formula II and Formula III are preferably first dissolved in organic solvents. For example, the Formula II acids may be first dissolved in a halogenated hydrocarbon, such as dichloromethane or chloroform, or ether while the Formula III alcohol may be first dissolved in an inert solvent, such as dimethylformamide, dimethylacetamide and the like. The reaction of II and III is carried out at a temperature of from about 0° to about 30° C., and preferably from about 5° to about 20° C., for a period of from about 12 to about 72 hours, and preferably from about 12 to about 48 hours.

The Formula II compound is employed in a molar ratio to the Formula III compound of 1:1.

The following Examples represent preferred embodiments of the invention. All temperatures are expressed in degrees centigrade (°C.).

EXAMPLE 1

(S)-1-(3-Mercapto-2-methyl-1-oxopropyl)-L-proline, (5,6-dihydro-5-oxopyrazolo[1,5—c]quinazolin-2-yl)-methyl ester

A.

(S)-1-[3-acetylthio)-2-methyl-1-oxo-propyl]-L-proline, (5,6-dihydro-5-oxopyrazolo[1,5—c]-quinazolin-2-yl)methyl ester To a solution formed of 7.1 g (0.033 M) of 2-(hydroxymethyl)pyrazolo[1,5—c]quinazolin-5-one (prepared as described in U.S. Pat. No. 4,112,096) in 300 cc DMF and 8.6 g (0.033 M) of 1-(3-acetylthio-2-methylpropanoyl)-L-proline (prepared as described in U.S. Pat. No. 4,105,776 in 250 cc $CH_2Cl_2$ at 5° C. is added a solution of 6.8 g (0.033 M) dicyclohexylcarbodiimide, (DCC) in 100 cc $CH_2Cl_2$ and 150 mg of 4-dimethylaminopyridine. The solution is allowed to stir at 0° for ½ hour; then at room temperature for about 72 hours. After stirring for 2 hours at room temperature, a crystalline precipitate begins to form. The solid is filtered to yield 2.7 g, m.p. 225°–230°, whose IR indicates it is dicyclohexylurea. The filtrate is concentrated to a small volume on the Rinco and about 500 cc $CH_2Cl_2$ is added to the viscous residue. The mixture is allowed to stand overnight and the solid filtered to yield 3.7 g solid, m.p. soft at 238°, clear at 270° whose I.R. indicates it is crude starting alcohol plus dicyclohexylurea. The filtrate is washed with 2×100 cc 0.5 N HCl, 1×150 cc saturated NaCl, 1×200 cc 5% $NaHCO_3$ and dried over $MgSO_4$. The solvent is removed and the viscous residue triturated with ether to yield 7.3 g (47.4%) product melting at 155°–160°. After recrystallization from $CH_3CN$ (3 g in 75 cc) the m.p. is 168°–169° and the weight 2.3 g.

B. (S)-1-(3-Mercapto-2-methyl-1-oxopropyl)-L-proline, (5,6-dihydro-5-oxopyrazolo-[1,5—c]quinazolin-2-yl)methyl ester A mixture of 4.56 g (0.01 M) of (S)-1-[3-(acetylthio)-2-methyl-1-oxopropyl]-L-proline, (5,6-dihydro-5-oxopyrazolo[1,5—c]-quinazolin-2-yl)-methyl ester and 200 cc 1.25 N of methanolic ammonia is stirred at room temperature under nitrogen for 2 hours. A clear solution forms after about 10 minutes. The solution is concentrated to dryness at 15 mm and 30° and the residue (4.4 g) dissolved in 250 cc 50% $CHCl_3$—$CH_2Cl_2$, washed with 2×150 cc $H_2O$ (to remove acetamide) and dried over $MgSO_4$. The solution is concentrated to yield 3 g (75%) product, m.p. 140°–142° d.

EXAMPLE 2

(S)-1-(3-Mercapto-2-trifluoromethyl-1-oxopropyl)-L-proline, (5,6-dihydro-5-oxopyrazolo[1,5—c]-quinazolin-2-yl)methyl ester

A.

(S)-1-[3-(Acetylthio)-2-(trifluoromethyl)-1-oxopropyl]-L-proline, (5,6-dihydro-5-oxopyrazolo[1,5—c]-quinazolin-2-yl)methyl ester Following the procedure of Example 1, part A, except substituting 1-[3-(acetylthio)-2-(trifluoromethyl)-propanoyl]-L-proline for 1-(3-acetylthiopropanoyl)-L-proline, the title A compound is obtained.

B.

(S)-1-(3-Mercapto-2-trifluoromethyl-1-oxopropyl)-L-proline, (5,6-dihydro-5-oxopyrazolo[1,5—c]quinazolin-2-yl)-methyl ester Following the procedure of Example 1, part B, except substituting for the Example 1A compound, the above Example 2A compound, the title compound is obtained.

EXAMPLE 3

(S)-1-[3-(Mercapto)-2,3-dimethyl-1-oxopropyl]-L-proline, (5,6-dihydro-5-oxopyrazolo[1,5—c]quinazolin-2-yl)methyl ester

A.

(S)-1-[3-(Acetylthio)-2,3-dimethyl-1-oxopropyl]-L-proline, (5,6-dihydro-5-oxopyrazolo[1,5—c]quinazolin-2-yl)-methyl ester Following the procedure of Example 1, part A, except substituting 1-(3-(acetylthio)-2,3-dimethylpropanoyl)-L-proline for 1-(3-acetylthio-2-methylpropanoyl)-L-proline, the title A compound is obtained.

B.

(S)-1-[3-(Mercapto)-2,3-dimethyl-1-oxopropyl]-L-proline, (5,6-dihydro-5-oxopyrazolo[1,5—c]quinazolin-2-yl)-methyl ester Following the procedure of Example 1, part B, except substituting for the Example 1A compound, the above Example 3A compound, the title compound is obtained.

EXAMPLE 4

(S)-1-(3-Mercapto-2-ethyl-1-oxopropyl)-L-proline, (5,6-dihydro-5-oxopyrazolo[1,5—c]quinazolin-2-yl)-methyl ester

A.

(S)-1-[3-(Acetylthio)-2-ethyl-1-oxopropyl]-L-proline, (5,6-dihydro-5-oxopyrazolo[1,5—c]quinazolin-2-yl)-methyl ester Following the procedure of Example 1, part A, except substituting 1-(3-acetylthio-2-ethylpropanoyl)-L-proline, for 1-(3-acetylthio-2-methylpropanoyl)-L-proline, the title A compound is obtained.

B. (S)-1-(3-mercapto-2-ethyl-1-oxopropyl)-L-proline, (5,6-dihydro-5-oxopyrazolo-[1,5—c]quinazolin-2-yl)methyl ester Following the procedure of Example 1, part B, except substituting for the Example 1A compound, the above Example 4A compound, the title compound is obtained.

EXAMPLE 5

(S)-1-(3-Mercapto-2-n-propyl-oxopropyl)-L-proline, (5,6-dihydro-5-oxopyrazolo[1,5—c]quinazolin-2-yl)-methyl ester

A.

(S)-1-[3-(Acetylthio)-2-n-propyl-1-oxopropyl]-L-proline, (5,6-dihydro-5-oxopyrazolo-[1,5—c]quinazolin-2-yl)methyl ester Following the procedure of Example 1, part A, except substituting 1-(3-acetylthio-2-n-propylpropanoyl)-L-proline for 1-(3-acetylthio-2-methylpropanoyl)-L-proline, the title A compound is obtained.

B.

(S)-1-(3-Mercapto-2-n-propyl-1-oxopropyl)-L-proline, (5,6-dihydro-5-oxopyrazolo-1,5—c]quinazolin-2-yl)methyl ester Following the procedure of Example 1, part B, except substituting for the Example 1A compound, the above Example 5A compound, the title compound is obtained.

EXAMPLE 6

(S)-1-(3-Mercapto-1-oxopropyl-L-proline, (5,6-dihydro-5-oxopyrazolo[1,5—c]quinazolin-2-yl)methyl ester A. (S)-1-[3-(Acethylthio)-1-oxopropyl]-L-proline, (5,6-dihydro-5-oxopyrazolo-[1,5—c]-quinazolin-2-yl)methyl ester Following the procedure of Example 1, part A, except substituting 1-(3-acetylthiopropanoyl)-L-proline for 1-(3-acetylthio-2-methylpropanoyl)-L-proline, the title A compound is obtained.

b. (S)-1-(3-Mercapto-1-oxopropyl-L-proline, (5,6-dihydro-5-oxopyrazolo[1,5—c]-quinazolin-2-yl)methyl ester Following the procedure of Example 1, part B, except substituting for the Example 1A compound, the above Example 6A compound, the title compound is obtained.

EXAMPLE 7

(S)-1-[3,3-(Mercapto)(ethyl)-1-oxopropyl]-L-proline, (5,6-dihydro-5-oxopyrazolo[1,5—c]quinazolin-2-yl)-methyl ester

A.

(S)-1-[3,3-(Acetylthio)(ethyl)-1-oxopropyl]-L-proline, (5,6-dihydro-5-oxopyrazolo[1,5c]quinazolin-2-yl)-methyl ester Following the procedure of Example 1, part A, except substituting 1-[3,3-(acetylthio)(ethyl)-thiopropanoyl]-L-proline for 1-(3-acetylthio-2-methyl-propanoyl)-L-proline, the title A compound is obtained.

B. (S)-1-[3,3-(Mercapto) (ethyl)-1-oxopropyl]-L-proline, (5,6-dihydro-5-oxopyrazolo-[1,5—c]quinazolin-2-yl)methyl ester Following the procedure of Example 1, part B, except substituting for the Example 1A compound, the above Example 7A compound, the title compound is obtained.

EXAMPLE 8

(S)-1-(3-Mercapto-2-methyl-1-oxopropyl-L-proline, (5,6-dihydro-5-oxopyrazolo[1,5—c]quinazolin-2-yl)-methyl ester

A.

(S)-1-[3-(Propanoylthio)-2-methyl-1-oxopropyl]-L-proline, (5,6-dihydro-5-oxopyrazolo[1,5—c]quinazolin-2-yl)-methyl ester Following the procedure of Example 1, part A, except substituting 1-(3-propanoylthio-2-methyl-propanoyl)-L-proline for 1-(3-acetylthio-2-methyl-propanoyl)-L-proline, the title A compound is obtained.

B. (S)-1-(3-Mercapto-2-methyl-1-oxopropyl-L-proline, (5,6-dihydro-5-oxopyrazolo-[1,5—c]quinazolin-2-yl)methyl ester Following the procedure of Example 1, part B, except substituting for the Example 1A compound, the above Example 8A compound, the title compound is obtained.

What is claimed is:

1. A compound of the structure $$R^1S-CH(R^2)-CH(R^3)-C(=O)-N\diagup\diagdown-COOCH_2-[\text{pyrazoloquinazolinone}]$$

wherein $R^1$ is hydrogen or lower alkanoyl, $R^2$ is hydrogen or lower alkyl and $R^3$ is hydrogen, lower alkyl or trifluoromethyl.

2. The compound as defined in claim 1 wherein $R^2$ is hydrogen and $R^3$ is lower alkyl.

3. The compound as defined in claim 2 wherein $R^1$ is hydrogen.

4. The compound as defined in claim 2 wherein $R^1$ is lower alkanoyl.

5. The compound as defined in claim 2 wherein $R^1$ is hydrogen or acetyl, $R^2$ is hydrogen and $R^3$ is methyl.

6. The compound as defined in claim 2 having the name (S)-1-[3-acetylthio]-2-methyl-1-oxopropyl]-L-proline, (5,6-dihydro-5-oxopyrazolo[1,5—c]-quinazolin-2-yl)methyl ester.

7. The compound as defined in claim 2 having the name (S)-1-(3-mercapto-2-methyl-1-oxopropyl)-L-proline, (5,6-dihydro-5-oxopyrazolo-[1,5—c]quinazolin-2-yl)methyl ester.

8. An anti-hypertensive composition comprising a compound as defined in claim 1 and a pharmaceutically acceptable carrier therefor.

9. A method for reducing blood pressure while inhibiting allergic reactions which comprises administering a compound as defined in claim 1 and a pharmaceutically acceptable vehicle therefor.

* * * * *

UNITED STATES PATENT AND TRADEMARK OFFICE
CERTIFICATE OF CORRECTION

PATENT NO. : 4,307,099
DATED : December 22, 1981
INVENTOR(S) : George B. Mackaness et al.

It is certified that error appears in the above-identified patent and that said Letters Patent are hereby corrected as shown below:

Column 7, line 3, after "propyl-" insert -- 1- --.

Signed and Sealed this

Twentieth Day of April 1982

[SEAL]

Attest:

GERALD J. MOSSINGHOFF

*Attesting Officer*     *Commissioner of Patents and Trademarks*